United States Patent [19]

Barcza

[11] 4,224,317
[45] Sep. 23, 1980

[54] SUBSTITUTED 1-OXA-4-AZA-2,6-DISILACYCLOHEXANES AND USE THEREOF

[75] Inventor: Sandor Barcza, Mt. Lakes, N.J.

[73] Assignee: Sandoz, Inc., E. Hanover, N.J.

[21] Appl. No.: 69,734

[22] Filed: Aug. 27, 1979

Related U.S. Application Data

[63] Continuation of Ser. No. 16,418, Mar. 1, 1979, abandoned.

[51] Int. Cl.² .................. C07F 7/10; A61K 31/695
[52] U.S. Cl. ...................................... 424/184; 544/69; 546/14; 549/4
[58] Field of Search ............... 544/69; 546/14; 549/4; 424/184

[56] References Cited

PUBLICATIONS

Hueckstaedt et al., "Chem. Abstracts", vol. 72 (1970), No. 37721y.

Primary Examiner—Henry R. Jiles
Assistant Examiner—R. W. Ramsuer
Attorney, Agent, or Firm—Gerald D. Sharkin; Robert S. Honor; Timothy G. Rothwell

[57] ABSTRACT

This disclosure describes compounds of the formula

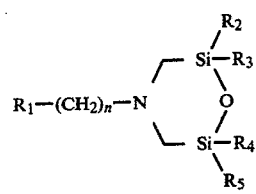

wherein
$R_1$ represents

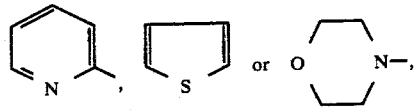

and
$R_2$, $R_3$, $R_4$ and $R_5$ each independently represent lower alkyl having 1 to 2 carbon atoms, and
n is 1 or 2,
which are useful as muscle-relaxant agents.

13 Claims, No Drawings

SUBSTITUTED 1-OXA-4-AZA-2,6-DISILACYCLOHEXANES AND USE THEREOF

This is a continuation of application Ser. No. 016,418 filed Mar. 1, 1979, abandoned.

This invention relates to substituted 1-oxa-4-aza-2,6-disilacyclohexanes which exhibit muscle relaxant activity. In particular, it relates to 2,2,6,6-tetramethyl-1-oxa-4-aza-2,6-disilacyclohexanes and pharmaceutically acceptable salts.

The compounds of this invention may be represented by the following structural formula

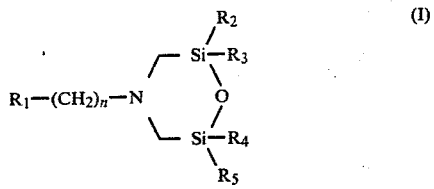

wherein
$R_1$ represents

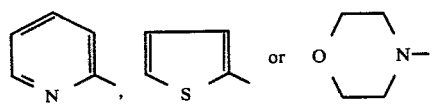

and
$R_2$, $R_3$, $R_4$ and $R_5$ each independently represent lower alkyl having 1 to 2 carbon atoms, i.e., methyl or ethyl, and
n is 1 or 2.

The compounds of formula (I) are prepared according to the following reaction scheme:

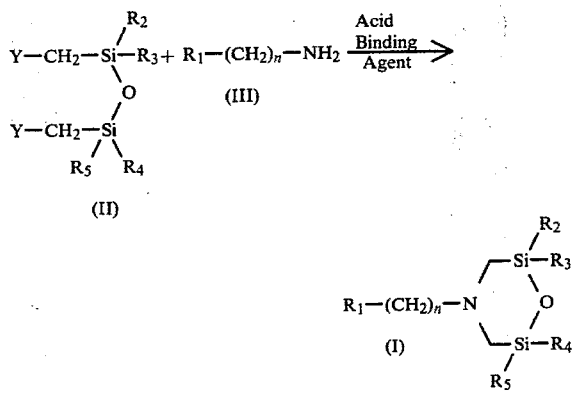

where
Y is a leaving group such as an arysulfonate or alkylsulfonate, e.g., tosylate or mesylate or iodo, bromo, chloro and the like, preferably iodo, and
$R_1$, $R_2$, $R_3$, $R_4$, $R_5$ and n are as defined above.

The compounds of formula (I) are prepared by reacting a compound of the formula (II) with a compound of the formula (III) in the presence of an acid binding agent. Although the particular acid binding agent employed is not critical, the preferred acid binding agents include pyridine, triethylamine, diisopropylmethylamine, alkali metal hydroxides or hydrides such as potassium hydroxide, sodium hydroxide, lithium hydride and the like, or an excess of a compound of formula (III), the latter being especially preferred. It is preferred that the reaction be carried out without a solvent, however, aprotic solvents such as acetonitrile, dimethylformamide, dimethylacetamide, and the like may be employed if the use of a solvent is desired. The temperature of the reaction is not critical, but it is preferred that the reaction be run from about −10° to 120° C., preferably from 20° to 90° C. The reaction is run from about 2 to 72 hours, preferably from about 5 to 18 hours. The product is recovered using conventional techniques, e.g., filtration and evaporation followed by distillation.

Many of the compounds of formulae (II) and (III) are known and may be prepared by methods described in the literature. The compounds of formulae (II) and (III) not specifically described in the literature may be prepared by analogous methods from known starting materials.

The preferred compounds of formula (I) are the compounds wherein $R_2$, $R_3$, $R_4$ and $R_5$ each represent methyl. Particularly, preferred compounds are those in which $R_1$ is

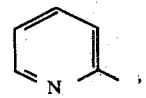

n is 1, and $R_2$, $R_3$, $R_4$ and $R_5$ each represent methyl.

The compounds of formula (I) are useful because they possess pharmacological activity in animals as muscle relaxants as indicated (1) by their activity in the rotorod tests as described by Dunham and Miya (J. Am. Pharm. Assoc., 45: 208, 1957), (2) by their ability to depress spinal reflexes measured by flexor and patellar responses using force displacement transducers in male cats given 1.0 to 3.0 milligrams per kilogram of animal body weight, i.e. of the test compound, and (3) by their ability to produce docility in behavior tests in mice given 25 to 200 mg/kg of animal body weight, p.o. of the test compound according to the 30-word adjective check sheet system basically as described by Irwin S. (Gordon Research Conference, Medicinal Chemistry, 1959), and Chen (Symposium on Sedative and Hypnotic Drugs, Williams and Wilkins, 1954).

The muscle relaxant effective dosage of the compounds of formula (I) will vary depending upon the particular compound employed. However, in general, satisfactory results are obtained when the compounds are administered orally at a daily dosage of from about 1.0 milligram to about 200 milligrams per kilogram of animal body weight, typically given in divided doses two to four times per day. For most large mammals, the total daily dosage is from about 10 to about 2000 milligrams and dosage forms suitable for internal administration comprise from about 2.5 to about 1000 milligrams of the compound in admixture with a solid or liquid pharmaceutical carrier or diluent.

For the above-mentioned use, the compounds may be administered orally in such forms as tablets, capsules, elixirs, suspensions and the like or parenterally in the form of injectable solutions or suspensions. The dosage will vary depending upon the mode of administration utilized and the compound employed.

The compounds of formula (I) may be similarly administered in the form of their non-toxic pharmaceutically acceptable salts. Such salts possess the same order of activity as the non-salt form and are readily prepared by reacting the molecule with an appropriate acid or an appropriate base by conventional technique, and accordingly, are included within the scope of this invention. Representative of such salts are the mineral acid salts, e.g., hydrochloride, hydrobromide, sulfate and the like.

Tablets and capsules containing the ingredients indicated below may be useful as muscle relaxants, in divided doses two to four times per day.

| Ingredients | Weight (mg.) | |
|---|---|---|
| | Tablet | Capsule |
| 4-(2-pyridylmethyl)-2,2,6,6-tetra-methyl-1-oxa-4-aza-2,6-disilacyclohexane | 200 | 200 |
| tragacanth | 10 | — |
| lactose | 247.5 | 300 |
| corn starch | 25 | — |
| talcum | 15 | — |
| magnesium stearate | 2.5 | — |
| | 500 mg. | 500 mg. |

EXAMPLE 1
4-(2-pyridylmethyl)-2,2,6,6-tetramethyl-1-oxa-4-aza-2,6-disilacyclohexane.

To 41.4 g. (0.1 mole) of 1,3-bis-iodomethyl-1,1,3,3-tetramethyl-disiloxane there is added dropwise with stirring 32.4 g. (0.3 mole) of 2-aminomethyl-pyridine while maintaining the temperature at 20° C. Stirring is continued at room temperature for 24 hours. The now heterogeneous mixture is combined with approximately 0.5 l. of toluene followed by approximately 0.5 l. of water. The equilibrated aqueous phase is then extracted with two 100 ml. portions of toluene. The combined organic phase is then washed twice with approximately 100 ml. of water to give 4-(2-pyridylmethyl)-2,2,6,6-tetramethyl-1-oxa-4-aza-2,6-disilacyclohexane as the crude free base.

The hydrochloride salt of the title compound is prepared by cooling the toluene solution of free base in ice and adding dropwise with stirring 10.0 g. (~0.1 mole) of concentrated hydrochloric acid. Cooling is continued and the resulting slurry is vigorously stirred for an additional fifteen minutes, filtered and liberally washed with toluene. The wet cake is then recrystallized from isopropanol (~100 to 150 ml.), filtered, washed, and dried to give the dihydrochloride; m.p. 214° to 217° C.

A small amount of the dihydrochloride may be recrystallized from isopropanol with extended boiling to give a sample of 4-(2-pyridylmethyl)-2,2,6,6-tetramethyl-1-oxa-4-aza-2,6-disilacyclohexane hydrochloride; m.p. 225° to 227° C. (dec).

The 4-(2-pyridylmethyl)-2,2,6,6-tetramethyl-1-oxa-4-aza-2,6-disilacyclohexane of this example is an effective muscle relaxant when orally administered to an animal in need of said treatment at a dosage of 100 mg. two to four times per day.

EXAMPLE 2
4-(2-thienylmethyl)-2,2,6,6-tetramethyl-1-oxa-4-aza-2,6-disilacyclohexane.

To a solution containing 22.6 g. (0.2 mole) of 2-thenylamine, 44.4 g. (0.44 mole) of triethylamine and 50.0 g. of acetonitrile dried over molecular sieves there is added 46.2 g. (0.2 mole) of 1,3-bis-chloromethyl-1,1,3,3-tetramethyl-disiloxane. The resulting homogenized solution is allowed to stand for 3 days and then heated in a bath at 90° C. for 36 hours. After cooling the mixture is then equiliberated between toluene and water, the organic phase is then washed with two more portions of water and concentrated to give 61.5 g. of a crude oil. Vacuum distillation through a Vigreux column gives 4-(2-thienylmethyl)-2,2,6,6-tetra-methyl-1-oxa-4-aza-2,6-disilacyclohexane; b.p. 78° to 80° C. at 0.1 to 0.11 mm.

The hydrochloride salt of the title compound is prepared by adding with stirring 31.5 g. (116 m mole) of 4-(2-thienylmethyl)-2,2,6,6-tetramethyl-1-oxa-4-aza-2,6-disilacyclohexane in 100 ml. of acetone to 11.6 ml. of concentrated hydrochloric acid in 50 ml. of acetone. To facilitate stirring for 10 minutes, more acetone is added to reach a total volume of 300 ml. The resulting slurry is filtered and washed twice with acetone. After drying in high vacuum at 70° C. overnight, there is obtained 4-(2-thienylmethyl)-b 2,2,6,6-tetramethyl-1-oxa-4-aza-2,6-disilacyclohexane hydrochloride; m.p. 251° to 252° C. (dec).

EXAMPLE 3
4-(2-N-morpholinoethyl)-2,2,6,6-tetramethyl-1-oxa-4-aza-2,6-disilacyclohexane.

A mixture of 26.0 g. (0.2 mole) of N-(2-aminoethyl) morpholine, 44.4 g. (0.44 mole) of triethylamine and 46.2 g. (0.2 mole) of 1,3-bis-chloromethyl-1,1,3,3-tetramethyldisiloxane is stirred at room temperature for 1 month. The mixture is then heated in a bath at 90° for 4 hours, and 20 ml. of dry acetonitrile and 20 ml. of triethylamine is added. Heating is continued for four additional hours. After cooling, the mixture is distributed between 1:1 ethylacetate:toluene and dilute aqueous sodium carbonate solution. The organic phase is washed with one more portion of sodium carbonate and two portions of water and then concentrated to give an oil crude product. The resulting oil is fractionally distilled through a Vigreux column to give 4-(2-N-morpholinoethyl)-2,2,6,6-tetramethyl-1-oxa-4-aza-2,6-disilacyclohexane; b.p. 90° to 94° C. at 0.08 to 0.11 mm.

Following the above procedure and using in place of 1,3-bis-chloromethyl-1,1,3,3-tetramethyldisiloxane, an equivalent amount of 1,3-bis-iodomethyl-1,1,3,3-tetramethyldisiloxane the reaction and heating time would be considerably less, for example 12 hours.

The dihydrochloride salt of the title compound is prepared by adding 34.3 g. (119 m mole) of 4-(2-N-morpholinoethyl)-2,2,6,6-tetramethyl-1-oxa-4-aza-2,6-disilacyclohexane in 200 ml. of acetone to 23.8 ml. of concentrated hydrochloric acid in 80 ml. of acetone. The resulting slurry is homogenized while being diluted with further amount of acetone totalling 450 ml., cooled to 0° C. overnight and filtered. The slurry is then washed twice with acetone and dried in high vacuum at 70° C. for 2 hours to give 4-(2-N-morpholinoethyl)-2,2,6,6-tetramethyl-1-oxa-4-aza-2,6-disilacyclohexane dihydrochloride; m.p. 272° (dec).

What is claimed is:

1. A compound of the formula

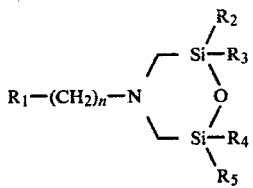

wherein

R₁ represents

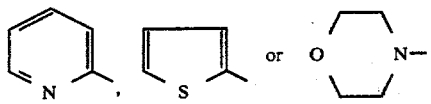

and

R₂, R₃, R₄ and R₅ each independently represent lower alkyl having 1 to 2 carbon atoms, and n is 1 or 2, or a pharmaceutically acceptable salt thereof.

2. A compound of claim 1 in free base form.

3. A compound of claim 1 in the hydrochloride salt form.

4. A compound of claim 1 in which R₂, R₃, R₄ and R₅ are methyl.

5. A compound of claim 1 in which R₁ is

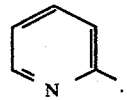

6. The compound of claim 1 which is 4-(2-pyridylmethyl)-2,2,6,6-tetramethyl-1-oxa-4-aza-2,6-disilacyclohexane.

7. The compound of claim 1 which is 4-(2-pyridylmethyl)-2,2,6,6-tetramethyl-1-oxa-4-aza-2,6-disilacyclohexane hydrochloride.

8. The compound of claim 1 which is 4-(2-thienylmethyl)-2,2,6,6-tetramethyl-1-oxa-4-aza-2,6-disilacyclohexane.

9. The compound of claim 1 which is 4-(2-thienylmethyl)-2,2,6,6-tetramethyl-1-oxa-4-aza-2,6-disilacyclohexane hydrochlroide.

10. The compound of claim 1 which is 4-(2-N-morpholinoethyl)-2,2,6,6-tetramethyl-1-oxa-4-aza-2,6-disilacyclohexane.

11. The compound of claim 1 which is 4-(2-N-morpholinoethyl)-2,2,6,6-tetramethyl-1-oxa-4-aza-2,6-disilacyclohexane dihydrochloride.

12. A method of treating muscle spasms which comprises administering to a mammal in need of said treatment a muscle relaxant effective amount of a compound according to claim 1.

13. A pharmaceutical composition for use as a muscle relaxant which comprises administering to a mammal in need of said treatment a muscle relaxant effective amount of a compound of claim 1 and a pharmaceutically acceptable carrier therefor.

* * * * *

UNITED STATES PATENT AND TRADEMARK OFFICE
CERTIFICATE OF CORRECTION

PATENT NO. : 4,224,317
DATED : September 23, 1980
INVENTOR(S) : Sandor Barcza

It is certified that error appears in the above–identified patent and that said Letters Patent are hereby corrected as shown below:

Column 4, line 22; before "2,2,6,6-tetramethyl-1-oxa-4-aza-", delete "4-(2-thienylmethyl)-b" and substitute therefor -- 4-(2-thienylmethyl)- --.

Column 6, Claim 9, line 3; delete "hydrochlroide" and substitute therefor --hydrochloride--.

Column 6, Claim 13, lines 2 and 3; delete "which comprises administering to a mammal in need of said treatment" and substitute therefor --comprising--.

Signed and Sealed this

Ninth Day of November 1982

[SEAL]

Attest:

GERALD J. MOSSINGHOFF

Attesting Officer     Commissioner of Patents and Trademarks